United States Patent [19]

Horii et al.

[11] 4,003,326
[45] Jan. 18, 1977

[54] APPARATUS FOR ASSEMBLING HULL MODULES FOR SHIPBUILDING

[75] Inventors: Hideharu Horii; Tadashi Orimoto, both of Ichiharashi, Japan

[73] Assignee: Mitsui Shipbuilding and Engineering Co., Ltd., Tokyo, Japan

[22] Filed: Dec. 3, 1974

[21] Appl. No.: 529,072

[30] Foreign Application Priority Data

Dec. 5, 1973  Japan .................. 48-138332

[52] U.S. Cl. .......................................... 114/65 R
[51] Int. Cl.² .......................................... B63B 3/00
[58] Field of Search ............ 114/65 R, 77 R, 77 A, 114/46; 61/64–68

[56] References Cited
UNITED STATES PATENTS

| | | | |
|---|---|---|---|
| 3,326,007 | 6/1967 | Burnett ................... | 61/66 |
| 3,429,288 | 2/1969 | Suit ...................... | 114/77 R |
| 3,453,833 | 7/1969 | Joosten ................... | 61/66 |
| 3,708,100 | 1/1973 | Buchfuhrer et al. ........ | 114/65 R |
| 3,854,435 | 12/1974 | Kinoshita ................ | 114/65 R |
| 3,875,887 | 4/1975 | Futtrup et al. ........... | 114/65 R |

FOREIGN PATENTS OR APPLICATIONS

195,343  12/1967  U.S.S.R. .................. 114/65 R

*Primary Examiner*—Trygve M. Blix
*Assistant Examiner*—Stuart M. Goldstein
*Attorney, Agent, or Firm*—Dorfman, Herrell and Skillman

[57] ABSTRACT

Apparatus for assembling hull modules for shipbuilding comprising two opposed chassis for supporting longitudinal assemblies and opposed second devices for supporting deck and bottom assemblies, all being constructed to be moved in the vertical and horizontal directions to adjust the position of the respective assemblies. The chassis is supported on cars by a plurality of interconnected oil cylinders adapted to enable the chassis to float on the oil in the cylinders and to permit both tilting and lateral displacement of the chassis on the cars.

2 Claims, 6 Drawing Figures

APPARATUS FOR ASSEMBLING HULL MODULES FOR SHIPBUILDING

The present invention relates to an apparatus for assembling hull modules for shipbuilding.

The object of the present invention is to provide an apparatus for supporting panel assemblies for welding each other to construct a module.

The other object of the present invention is to provide an apparatus for supporting panel assemblies which is of simplified construction.

The present invention will be explained with reference to the accompanying drawings, in which.

Figure 1:
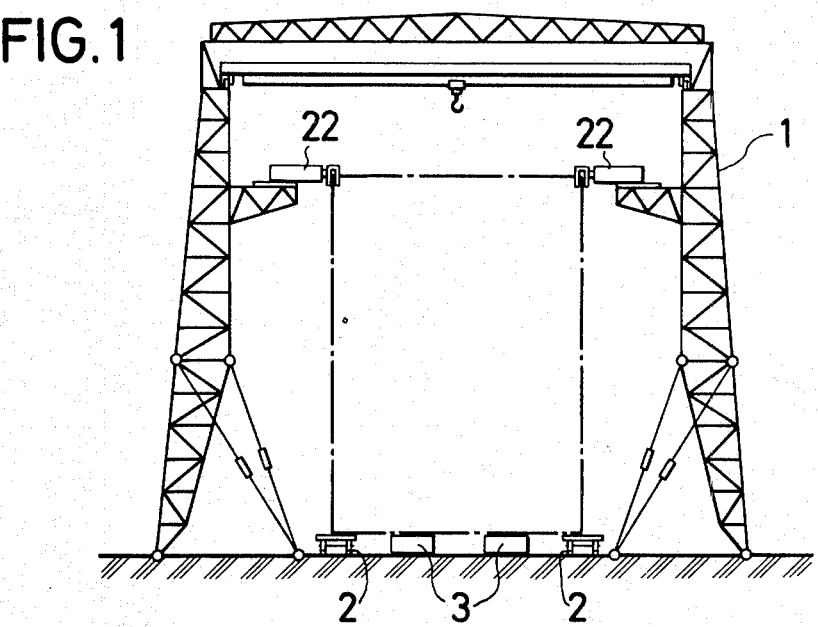
FIG. 1 is a front view showing an apparatus according to the present invention.

Referring to the drawings and more particularly to FIG. 1, a framework 1 is provided for assembling hull modules and there are provided opposed rails 2, four end supporting devices 3, and four intermediate supporting devices 4. Each supporting device 3 as shown schematically in FIG. 2 comprises horizontally movable plates 50 and 51 and a vertically movable plate 52 which are provided in superimposed relation.

Figure 3:
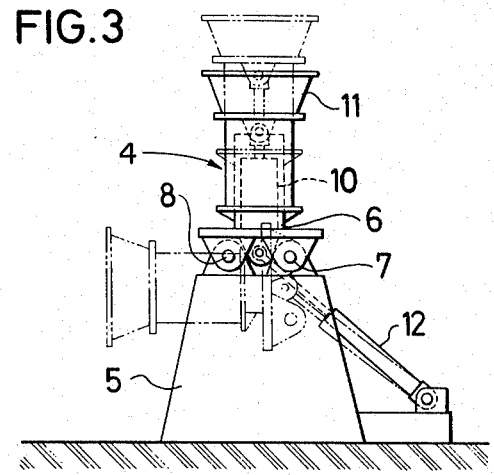
FIG. 3 is a side view illustrating a supporting device shown in FIG. 2.

The plate 50 may be moved by hydraulic cylinder means 53, the plate 51 may be moved transversely on the plate 50 and the plate 52 is raised and lowered on the plate 51. Consequently, the upper plate 52 can be moved in the horizontal and vertical directions by combining the motions of three plates. The supporting device 4 is, as detailed in FIG. 3, constructed to be vertically moved. A support 6 of the device is pivotally mounted on the base 5 by a horizontal pin 7 so that the support may be rotated to the horizontal position as shown by dotted chain line, and a pin 8 is inserted to keep the support 6 upright. An oil hydraulic cylinder 10 is provided inside the support 6 and the piston rod thereof is connected to a receiving block 11 on the support. Rotation of the support 6 is caused by an oil hydraulic cylinder 12, of which piston rod is connected to the support 6 at the position between the pins 7 and 8 and the cylinder is connected to the ground. Accordingly, when the pin 8 is removed and the piston rod of the cylinder 12 is retracted, the support 6 is rotated and laid down as shown in chain line.

Figure 4:
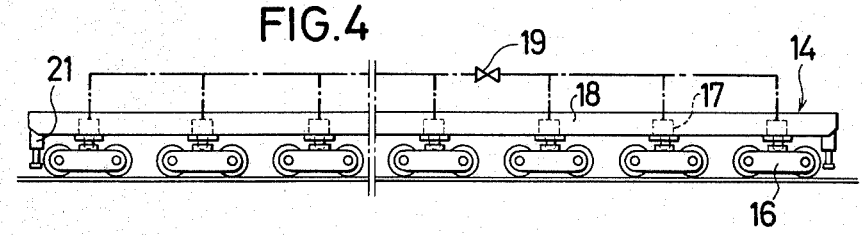
FIG. 4 is a side view showing a car.
Figure 5:
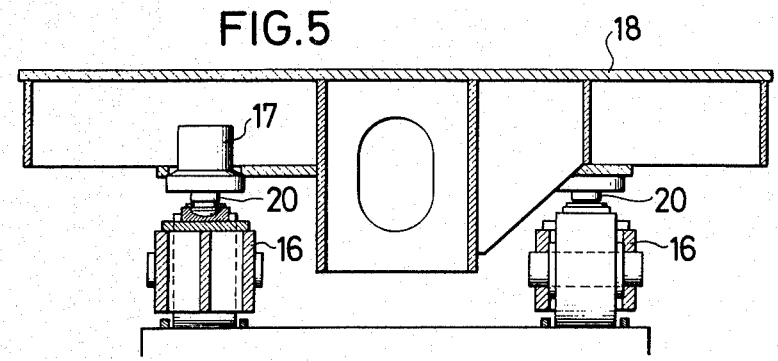
FIG. 5 is a sectional view showing the chassis of the car.

On the rails 2 there are cars 14 each of which is connected to a power car 15. The car 14 comprises a chassis 18 supported by a plurality of oil hydraulic cylinders 17 each of which is vertically provided on the frame 16 provided with a pair of wheels in FIG. 4. As shown in FIG. 5, the plunger 20 of the cylinder has a spherical end which is mounted on the spherical seat of the frame 16. Further, the car 14 is so constructed that the chassis 18 may be slightly moved in the lateral direction by external force. On both forward and rearward ends of the car, oil cylinders 21 are vertically provided to incline the chassis 18. All cylinders 17 are connected each other and valve 19 is provided in the piping.

Figure 6:
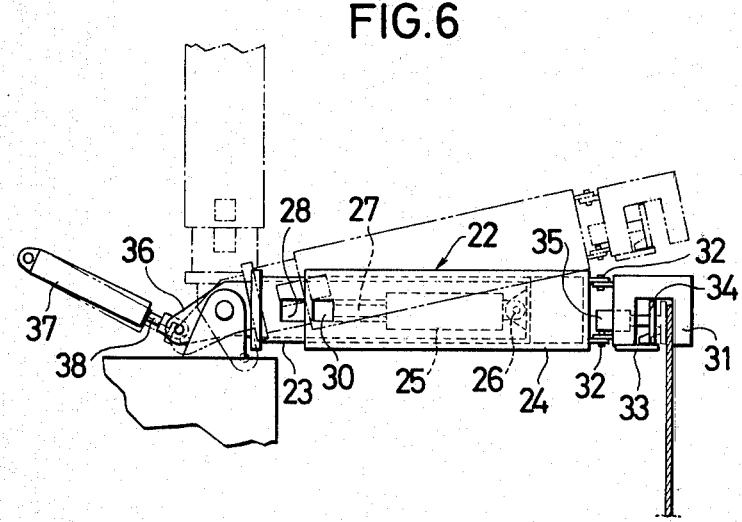
FIG. 6 is a side view showing a holding device.

As shown in FIG. 1, holding devices 22 are symmetrically provided on the upper portion of the framework 1. As shown in FIG. 6, the holding device 22 comprises a base, inner cylinder 23 rotatably provided on the framework 1 and an outer cylinder 24 slidably engaged with the inner cylinder 23. An oil hydraulic cylinder 25 is provided in the inner cylinder 23. The base portion of the cylinder 25 is connected to the end of the inner cylinder by a pin 26 and the end of the piston rod 27 is fixed to the outer cylinder 24 by a piece 30 passing through an elongated slit 28 of the inner cylinder. To the end of the outer cylinder, a gripping device 31 is connected by vertical pins 32 so as to be rotated in the horizontal plane. The gripping device has a U-shaped body and a gripping piece 34 is slidably provided on the lower side plate 33 and the rod of the hydraulic cylinder 35 is connected thereto. Thus, the gripping piece 34 may be slided to grip the panel assembly. There is a bracket 36 projecting from the base portion of the inner cylinder 23. To this bracket is connected a piston rod 38 of an oil hydraulic cylinder 37 which is mounted on the framework 1 by a pin, so that the holding device may be rotated in the vertical plane as shown by broken lines in FIG. 6.

Figure 2:
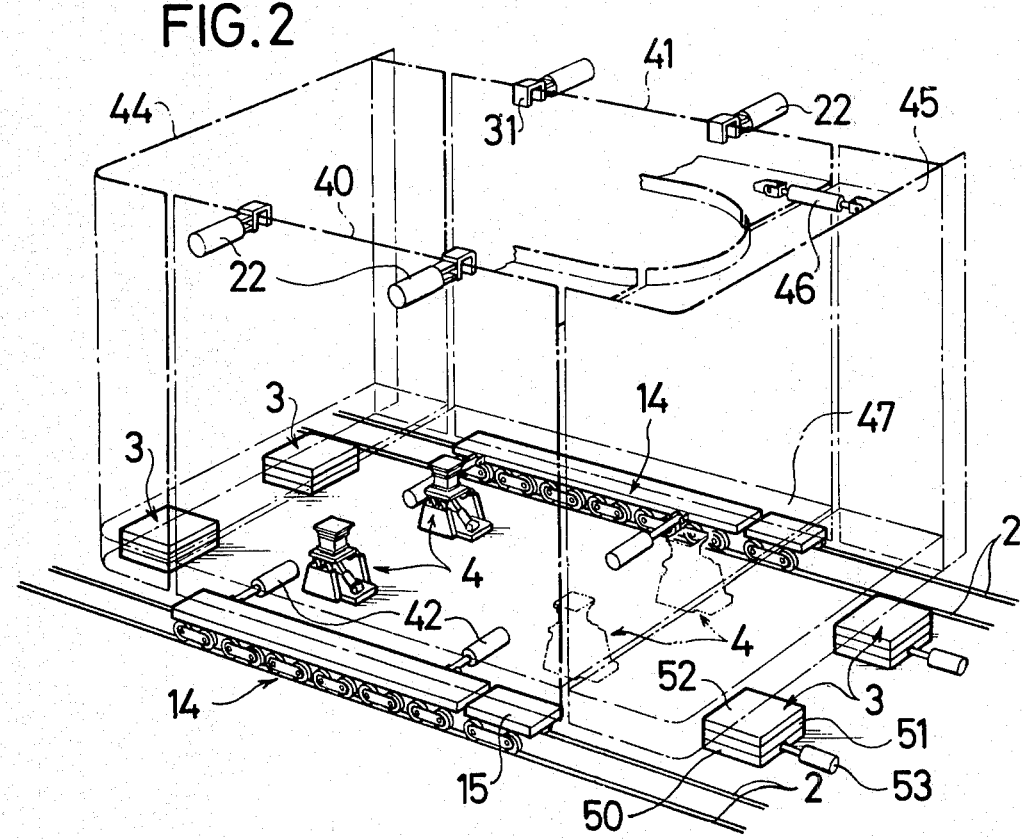
FIG. 2 is a perspective view schematically showing the apparatus.

In operation, each holding device 22 is held upright by operating the oil hydraulic cylinder means 37 oil hydraulic cylinder means 42 is provided between the side of the chassis 18 of the cars 14 and the ground as shown in FIG. 2. Then a side panel assembly 40 and a longitudinal bulkhead assembly 41 which are to be assembled into a wing tank of a tanker, are placed on the cars 14 by operating a crane, and subsequently each holding device is downwardly rotated to the horizontal position as shown in FIG. 2. Thereafter the gripping piece 34 is moved to grip the side panel assembly 40 and the longitudinal bulkhead assembly 41. In order to adjust the vertical position of each panel assembly, cylinders 25 are operated to move the outside cylinder 24 to move the top of the panel assembly and the cylinders 42 are operated to move laterally the chassis 18 to move the bottom of the panel assembly. And then the valve 19 (FIG. 4) is opened and oil cylinders 21 are operated to adjust the inclination of the panel assemblies. In this operation all oil cylinders 17 are communicated with each other, therefore, the chassis 18 is in the state of floating on the oil in cylinders 17. Accordingly, by applying low pressure oil to the oil cylinder 21, the chassis may be easily tilted. Each intermediate supporting device 4 is erected by operating the cylinder 12 and the oil cylinder 10 is operated to rise the receiving block 11. A transverse member 47 is placed on the erected receiving blocks 11.

Then, an upper deck assembly 44 and a bottom assembly 45 of the wing tank are placed on the supporting devices 3. Each assembly is connected to the side panel assembly 40 or the longitudinal bulkhead assembly 41 by oil cylinders 46 at the top thereof. Each plate of the supporting device 3 is vertically or horizontally moved so that the position of the assembly may be adjusted by combining with the operation of the oil cylinder 46. In the above manner, all assemblies are assembled and the transverse member welded at joints, thus completing assembling.

Subsequently, holding devices 22 are released and moved to the upright position by operating the oil cylinder 37. Oil cylinders 42 and 46 are removed and supporting devices 4 are laid down by operating the oil cylinders 12, and the supporting devices 3 are lowered.

Thus the hull module is supported on the cars 14. Accordingly, a completed hull module is carried by the cars to the succeeding step of the shipbuilding.

It will be understood from the foregoing that the hull module may be assembled readily and accurately according to the present invention.

What is claimed is:

1. Apparatus for assembling hull modules for shipbuilding, including upright, longitudinal assemblies, an upright deck assembly and a bottom assembly, comprising opposed cars to support a pair or upright longitudinal assemblies respectively at their bottom portions, said each car having a chassis adapted to be moved in the vertical and horizontal directions, opposed supporting means to support upright deck assembly and bottom assembly respectively and operable to be moved in the vertical and horizontal directions to permit assembly thereof with said longitudinal assemblies, and means to grip upper portions of said longitudinal assemblies and operable to be retracted from the gripping position, each car chassis being supported by a plurality of vertical oil cylinders which are communicated with each other through a common valve which is opened to enable the chassis to float on the oil in the cylinders and to permit tilting of the chassis, and separate oil cylinders to adjust the longitudinal tilt of said chassis and to laterally displace the chassis.

2. Apparatus according to claim 1 including tracks for said opposed cars, said tracks extending longitudinally below and upright longitudinal assemblies, and separate extendable supporting devices mounted intermediate said tracks and intermediate said opposed supporting means for said deck and bottom assemblies.

* * * * *

UNITED STATES PATENT OFFICE
CERTIFICATE OF CORRECTION

Patent No. 4,003,326            Dated January 18, 1977

Inventor(s) Hideharu Horii and Tadashi Orimoto

It is certified that error appears in the above-identified patent and that said Letters Patent are hereby corrected as shown below:

Claim 2, line 3, "and" (first occurrence) should be --said--.

Signed and Sealed this

Third Day of May 1977

[SEAL]

Attest:

RUTH C. MASON
*Attesting Officer*

C. MARSHALL DANN
*Commissioner of Patents and Trademarks*